Figure 1:
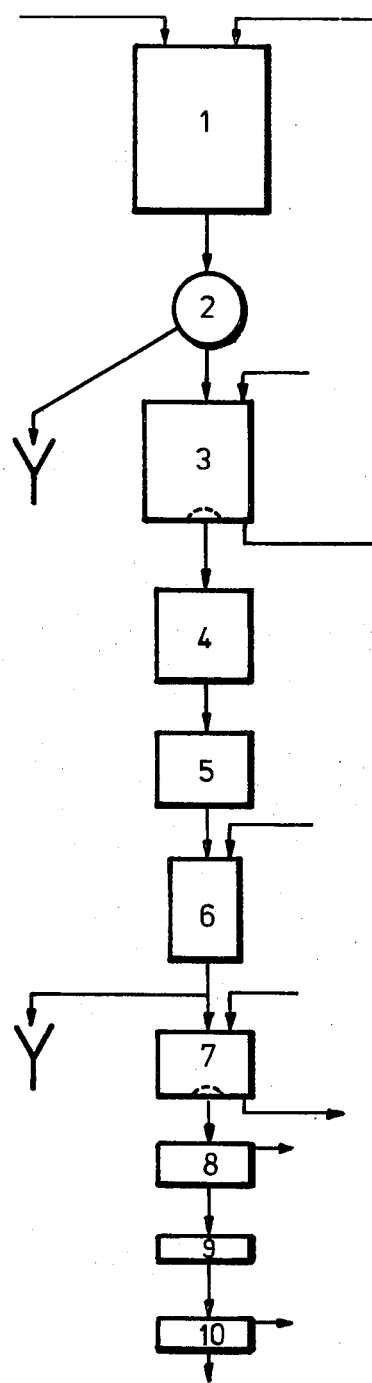

United States Patent [19]

Rauenbusch et al.

[11] 4,174,439
[45] Nov. 13, 1979

[54] PROCESS FOR ISOLATING GLUCOPYRANOSE COMPOUND FROM CULTURE BROTHS

[75] Inventors: Erich Rauenbusch; Delf Schmidt, both of Wuppertal, Fed. Rep. of Germany

[73] Assignee: Bayer Aktiengesellschaft, Leverkusen, Fed. Rep. of Germany

[21] Appl. No.: 898,263

[22] Filed: Apr. 20, 1978

[30] Foreign Application Priority Data

May 4, 1977 [DE] Fed. Rep. of Germany ....... 2719912

[51] Int. Cl.$^2$ .......................................... C07H 15/20
[52] U.S. Cl. .......................................... 536/18; 536/1; 536/4; 536/17 R
[58] Field of Search ....................................... 536/1, 18

[56] References Cited

U.S. PATENT DOCUMENTS

| | | |
|---|---|---|
| 3,876,766 | 4/1975 | Frommer et al. .......................... 536/1 |
| 4,062,950 | 12/1977 | Frommer et al. .......................... 536/18 |
| 4,065,557 | 12/1977 | Frommer et al. .......................... 536/1 |

Primary Examiner—Johnnie R. Brown
Assistant Examiner—Blondel Hazel
Attorney, Agent, or Firm—Sprung, Felfe, Horn, Lynch & Kramer

[57] ABSTRACT

The invention relates to a process for isolating O-{4,6-dideoxy-4-[[1S-(1,4,6/5)-4,5,6-trihydroxy-3-hydroxymethyl-2-cyclohexen-1-yl]-amino]-α-D-glucopyranosyl}-(1→4)-O-α-D-glucopyranosyl-(1→4)-D-glucopyranose from culture broths such as are obtained by fermenting micro-organisms of the family Actinoplanaceae, especially of strains of the genus Actinoplanes involving the use of ion exchangers.

17 Claims, 1 Drawing Figure

PROCESS FOR ISOLATING GLUCOPYRANOSE COMPOUND FROM CULTURE BROTHS

The present invention relates to a new, advantageous process for isolating 0-{4,6-dideoxy-4-[[1S-(1,4,6,/5)-4,5,6-trihydroxy-3-hydroxymethyl-2-cyclohexen-1-yl]-amino]-α-D-glucopyranosyl}-(1→4)-0-α-D-glucopyranosyl-(1→4)-D-glucopyranose from culture broths such as are obtained by fermenting micro-organisms of the family Actinoplanaceae, especially of strains of the genus Actinoplanes. Cultures of the following strains had been deposited in the "Centralbureau vor Schimmelcultures" at Baarn/Netherlands: SE 50 (CBS 961.70), SB 18 (CBS 957.70), SE 82 (CBS 615.71), SE 50/13 (CBS 614.71) and SE 50/110 (CBS 674.73).

The teaching of DT-OS (German Published Specification) No. 2,064,092 is that a number of Actinomycetes form inhibitors for glycoside hydrolases, preferably enzymes of the digestive tract which split carbohydrates. One group of these inhibitors is relatively stable towards heat and is stable towards acid and alkali at room temperature. From a chemical point of view, these inhibitors belong to the oligosaccharide or polysaccharide class.

In the pure form, some of these inhibitors exhibit an exceptionally powerful inhibition of saccharase.

The title compound of the formula I

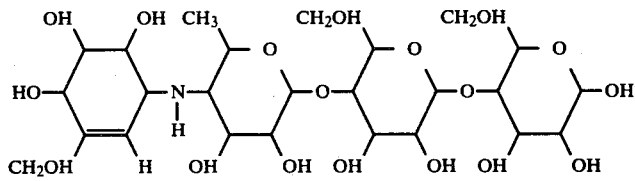

is a particularly active saccharase inhibitor. (DT-OS (German Published Specification) No. 2,347,782).

These inhibitors could hitherto be isolated in the pure form from the culture broths of the fermentation only using very troublesome concentration and purification processes, since components which are very similar chemically and physically (homologues), but which have a less powerful saccharase-inhibiting action and on the other hand, a more powerful amylase-inhibiting action, are also formed in the course of the fermentation.

Thus, the amino-sugar derivative of the formula I is obtained, according to DT-OS (German Published Specification) No. 2,347,782, via the following stages, processing of the entire fermentation volume over several steps being necessary in some cases:

1. Separation of the mycelium,
2. Decolorisation of the culture solution,
3. Adsorption of the inhibitor mixture on active charcoal,
4. Desorption from the charcoal using suitable organic solvents,
5. Adsorption of the charcoal desorbate on strongly acid cation exchangers in order to separate off inert saccharides,
6. Desorption of the cation exchanger using dilute ammonia,
7. Concentration of the desorbate,
8. Lyophilisation or precipitation of the concentrate,
9. Fine purification of this 30–50% pure crude product by molecular sieve chromatography (for example over Biogel) and
10. Combining of the active fraction, concentration and precipitation or lyophilisation.

These troublesome purification processes mean that the activity yield of the compound of the formula I is only about 20%. Since the capacity of molecular sieve chromatography is also very limited (0.5 g of crude inhibitor per 5 cm×95 cm column), very many column separations are necessary in order to obtain adequate amounts of the compound.

The present invention relates to a new process for isolating an amino-sugar derivative which is 0-{4,6-dideoxy-4[[1S-(1,4,6,/5)-4,5,6-trihydroxy-3-hydroxymethyl-2-cyclohexen-1-yl]-amino]-α-D-glucopyranosyl}-(1→4)-0-α-D-glucopyranosyl-(1→4)-D-glucopyranose from a culture broth obtained by fermenting a micro-organism of the family Actinoplanaceae, in particular of a strain of the genus Actinoplanes, in which: (a) a mixture of a strongly acid cation exchange resin and an anion exchange resin in the acid or basic form is added to the culture broth, preferably without the mycelium being previously separated off, (b) the resin mixture is separated off from the culture filtrate and from any mycelium that may be present and desirably washed, (c) the separated off resin mixture is treated with at least one cation-containing dilute solution so as to elute the amino-sugar derivative, (d) the resulting eluate is passed over a combination of a highly crosslinked strongly acid cation exchanger, which weakly bonds the amino-sugar derivative, in the H⊕ form and an anion exchanger in the basic form, (e) the eluate is then passed over a strongly acid cation exchanger, which bonds the amino-sugar derivative strongly, in the H⊕ form, (f) the cation exchanger with the amino-sugar derivative bonded thereto is desirably washed usually with water, and is treated with from 0.01 to 0.05 N mineral acid so as fractionally to elute material bound to the exchanger in a plurality of fractions, (g) the fraction(s) containing said amino-sugar derivative is (are) recovered, the fraction(s) being conveniently brought to a pH value of from 5 to 7, and desirably concentrated, filtered and dried.

In the following text, the individual process steps according to the invention are further explained in the same sequence as in the preceding paragraph.

Suitable fermentation broths which can be employed are known, for example, from DT-OS (German Published Specification) No. 2,347,782. In addition to from 20 to 30% of mycelium and other constituents, these contain the amino-sugar derivative of the formula I, preferably in a concentration of from 50,000 to 100,000 SIU/l of solution (SIU=saccharase inhibitor unit(s)). After removing the mycelium 15 m³ of fermentation broth give 11–12 m³ of solution with an active compound content of 600–1,000 MSIU. The saccharase inhibitions is determined by the method published in DT-OS (German Published Specification) No. 23 47 782 1 MSIU equals 1·10⁶ SIU.

In the adsorption step (a), the culture broth is treated with a strongly acid cation exchange resin in the acid form and at the same time with an anion exchange resin in the basic form, preferably without the mycelium being previously separated off. Cation exchangers based on polystyrene which are crosslinked to the extent of from 2 to 6%, preferably from 3 to 4%, have proved particularly suitable for this adsorption step. Examples which may be mentioned of particularly suitable cation exchangers are: Lewatit ® S 1040 W, Lewatit ® SC 104 and Lewatit ® TSW 40. Weakly basic exchangers based on polystyrene, such as, for example, Lewatit ® MP 62, are particularly suitable anion exchangers.

Anion exchangers based on phenol formaldehyde resins or amino alcohol derivatives of polyacrylicacid or polymethacrylicacid may also be used.

It has been shown that adsorption of the amino-sugar derivative of the formula I on a cation exchanger in the Na$^\oplus$ form and NH$_4^\oplus$ form analogous to the smooth adsorption of structurally related aminoglycoside antibiotics, such as streptomycin, is not possible. Even when a cation exchanger in the H$^\oplus$ form is employed by itself, only slight adsorption can be achieved. However, surprisingly, 80 to 95% adsorption is possible if a cation exchanger in the acid form and an anion exchanger in the basic form are employed simultaneously.

The resin mixture is separated off from the culture filtrate (step b) and, if appropriate, also from the mycelium in the customary manner. After the separation, the ion exchange resin, which carries the active compound of the formula I, can be washed with deionised water and thus be free from any adhering impurities in an industrially simple manner.

The elution of the amino-sugar derivative of the formula I according to process step (c) can also be realised in an industrially simple manner. The elution can be carried out with the most diverse cation-containing solutions, such as acids, bases and salt solutions. It is advisable to use elution solutions of as low a concentration as possible, and the minimum concentration which just still leads to complete elution of the adsorbed amino-sugar derivative can be determined without difficulty in preliminary experiments. The elution can be carried out particularly gently and selectively with dilute salt-containing solutions, preferably solutions of the alkali metal salts, alkaline earth metal salts and/or ammonium salts of weak acids, for example dilute sodium acetate solutions or calcium acetate solutions, which can contain bases or acids, such as, for example, ammonia solution or acetic acid. Diluted bases especially weak bases such as ammonia and diluted acids expecially weak acids as acetic acid both in concentrations from 0.02 M to 0.2 M can also be used, but the amount of impurities in the eluate is higher than with the elution by salt.

The salt solutions are preferably used at a concentration in the range of from 0.05 to 0.2 M in the case of monovalent cations, and in the range of from 0.025 to 0.10 M in the case of divalent cations.

In process step (d), the eluate is passed over a combination of a highly crosslinked, strongly acid cation exchange resin, which scarcely bonds the amino-sugar derivative, in the H$^\oplus$ form, and then with an anion exchange resin in the basic form, which are conveniently arranged in superposed layers in a column. The exchange resins can, of course, also be used in separate columns connected in series. A synthetic exchange resin which is based on polystyrene and has a degree of crosslinking of from 7 to 20%, preferably from 8 to 15%, is desirably used as the cation exchanger in step (d); Lewatit ® S 100 may be mentioned as an example. Further suitable cation exchange resins can be determined in simple preliminary experiments by testing their bonding capacity for the amino-sugar derivative of formula I. In principle, any desired anion exchange resin can be chosen; surprisingly, weakly basic anion exchange resins, such as, for example, Lewatit ® MP 62, a macroporous, monofunctional, weakly basic anion exchange resin based on polystyrene, have proved to be particularly effective. In the case of the anion exchange resins, synthetic exchange resins should also preferably be used.

The actual separation of the amino-sugar derivative of the formula I from other components, in particular homologuous compounds, is effected in process step (e). For this, the eluate obtained after the desalination in step (d) is passed over a strongly acid cation exchange resin, which bonds the amino-sugar derivative strongly in the H$^\oplus$ form. Cation exchange resins which are based on polystyrene and have a low degree of cross-linking of about 2 to 6%, such as, for example, Lewatit ® TSW 40, Lewatit ® SC 104 and Lewatit ® S 1040 W, have proved particularly suitable for the separation by chromatography.

The exchange resin with the amino-sugar derivative of formula I bonded thereto is then fractionally eluted (f) with from 0.01 to 0.1 N mineral acids, preferably 0.025 N hydrochloric acid. Those fractions of the eluate containing the desired amino-sugar derivative are desirably brought to a pH value of about 5 to about 7 by adding bases or with an anion exchanger in the basic form, and then may be concentrated, filtered and dried.

Compared with the process known from the literature for isolating the amino-sugar derivative, the process according to the invention, has a number of surprising advantages, and is particularly suitable for preparing the compound industrially and is highly economical.

It has already been mentioned that, surprisingly, an 80 to 90% adsorption of the amino-sugar derivative can be achieved in adsorption step (a) by a combination of a cation exchanger in the acid form and an anion exchanger in the basic form.

In addition, it should be mentioned that the separation of the mycelium from the fermentation solution can be dispensed with. Depending on the mycelium content, this separation step presents great industrial difficulties, since because of the high proportion of solids, the separators must be very frequently backwashed, losses being unavoidable. The separation of the mycelium using a decanter is incomplete.

Compared with the use, known from DT-OS (German Published Specification) No. 2,347,782, of active charcoal powder, the use of the granular exchange resins as the adsorbent has the advantage of being cleaner and more convenient to handle. The bonding capacity of the granular active charcoal, which can be more acceptably processed, is too low. Moreover, once the charcoal has been desorbed it must be discarded, in contrast to which the ion exchange resins can be regenerated and frequently re-used. It is necessary to use inflammable organic solvents (for example acetone) for the elution of the active compound from the active charcoal; on the other hand, the mixture of ion exchangers is normally eluted with aqueous solutions.

Decolorisation of the eluate obtained in process step (c), for example with active charcoal or adsorption resins, such as is advised according to the procedure of DT-OS (German Published Specification) No. 2,064,092, can be dispensed with in the process according to the present invention.

The separation of the homologues which takes place in process step (e) is particularly advantageous industrially. Thus, the exchanger columns used, according to the invention, for the separation of the homologues have a separation capacity about 40 times higher than the molecular sieves used in the chromatography according to the procedure of DT-OS (German Published Specification) No. 2,347,782.

Thus, 500 mg of crude product can be separated on a column containing a bed of 2 l of a molecular sieve (Biogel ® P 2), whilst 20 g can be separated over a column containing 2 l of a strongly acid cation exchanger (for example Lewatit ® SC 104).

Altogether, compared with the procedure known from DT-OS (German Published Specification) No. 2,347,782, the process according to the invention shows an improvement of yield from 20% to from 50 to 60% and is an industrially decidedly simplified procedure for the preparation of the amino-sugar derivative, which is distinguished by the fact that the expenditure on labour is lower, the expenditure on materials is lower, no organic solvents are used and there is the possibility of using a continuous procedure and of regenerating the ion exchangers and being able to re-use them.

FIG. 1 shows a flow chart for the industrial isolation of the title compound from culture broths. The strongly acid cation exchanger and the anion exchanger are introduced into the fermentation broth, containing mycelium, in a tank (1). The mixed ion exchange resin is separated off from the fermentation broth, containing mycelium, via a sieve screw centrifuge (2). The ion exchange resin, with the adsorbed amino-sugar derivative, can thereby be rinsed in the machine with deionised water. For the elution, the ion exchange resin is introduced into a kettle (3) provided with nozzle sieves, and the amino-sugar derivative is then eluted by adding a dilute salt solution. The solution flowing out is freed from small and strongly basic cations in a column using a highly crosslinked, strongly acid cation exchanger (4) which weakly bonds the amino-sugar derivative, and the strongly acid solution is then brought again to a pH value above 3 in a column using an anion exchanger in the basic form (5).

The desalinated solution is now discharged onto a column containing a strongly acid cation exchanger, which bonds the amino-sugar derivative strongly, in the H⊕ form (6), the amino-sugar derivative becoming concentrated in the upper parts of the column. The column is rinsed with a little deionised water and separation of the various components is started, preferably with dilute hydrochloric acid. The eluate is collected in fractions and analysed with respect to the amino-sugar derivative. The fractions containing the amino-sugar derivative of the formula I are combined.

The fractions containing the amino-sugar derivative are brought to a pH value of from 6.0 to 6.5 in a container (7) by adding an anion exchanger in the basic form, and the solution is concentrated in vacuo (8) and sterilized by filtration and freeze-dried or spray-dried in appropriate apparatus (9,10).

Adsorption

In examples 1–5 the fermentation of the Actinoplanes strain SE 50/110 (CBS 674.73) was done according to the disclosure in DT-OS (German Published Specification) No. 2,347,782, example 10.

EXAMPLE 1

50 g of a cation exchange resin (Lewatit ® S 1040 W) in the H+ form and 30 g of an anion exchanger (Lewatit ® M 600) in the OH form were added to 300 ml of a culture broth with a mycelium content of 25% and an inhibitor content of 50 SIU/ml in the solution. The mixture was stirred at room temperature for 50 minutes. The solution, containing the mycelium, was filtered through a sieving nozzle with 0.1 mm slits. For testing, a sample of the filtered broth was centrifuged and was examined for saccharase inhibitor in the supernatant liquor. The solution still contained 2.5 SIU/ml, that is to say 5%, of the starting activity.

The ion exchangers were filtered off in the swollen state and this moist product was weighed out.

In order to examine the adsorption procedure, the exchanger mixture with the adsorbed amino-sugar derivative was filled into a column and washed with 100 ml of water and the inhibitor was eluted with 200 ml of 0.1 M sodium chloride solution. 205 ml of eluate were obtained, with an activity of 44 SIU/ml, that is to say a total of 9020 SIU. The starting activity in 300 ml of the culture broth or, after removing the mycelium, in 225 ml of the culture solution, was 11,250 SIU. The yield of inhibitor which could be eluted was 80%.

EXAMPLE 2

27 g of Lewatit ® S 1040 W (H+ form) and 4 g of Lewatit MP 62 (basic form) were added to 300 ml of a culture broth with a mycelium content of 28% and an inhibitor content of 74 SIU/ml, whilst stirring continuously. After 30 minutes, the resin was filtered off as described in Example 1 and rinsed with 50 ml of water. After removing the mycelium, the broth still contained 5.3 SIU/ml. In the case of a volume of 245 ml of solution, this was 1,300 SIU, or 8.1% of the activity employed of 16,000 SIU.

EXAMPLE 3

10 g of Lewatit ® S 100 (H+ form) and 11 g of Lewatit ® M 500 (OH form) were added to 100 ml of a culture broth with a mycelium content of 28% and an inhibitor content of 74 SIU/ml, whilst stirring continuously. After 30 minutes, the resin was filtered off as described in Example 1. After removing the mycelium, the broth still contained 71 SIU/ml. In the case of a volume of 68 ml, this was 4,800 SIU, or 90% of the activity employed of 5,330 SIU. The inhibitor was thus adsorbed onto this ion exchanger only to a very slight extent.

EXAMPLE 4

18 g of Lewatit ® SC 104 (H+ form) and 9 g of Lewatit ® MP 62 were added to 200 ml of a culture broth with a mycelium content of 22% and an inhibitor content of 61 SIU/ml, whilst stirring continuously. After 100 minutes, the resin was filtered off as described in Example 1. After separating off the mycelium, the broth contained 7.5 SIU/ml. In the case of a volume of 150 ml, this was 1,125 SIU, or 12% of the activity employed of 9,520 SIU.

EXAMPLE 5

1,600 l of a fermentation broth with a mycelium content of 22% give a solution volume of 1,248 1. The inhibitor content was 65 SIU/ml. The starting content is thus 81.1 MSIU. The fermentation broth was stirred, and 200 l of Lewatit ® SC 104 (Hform) and 90 l of Lawatit ® MP 62 (basic form) were added at room temperature in the course of one hour. The mixture is subsequently stirred for a further 2 hours and a sample is removed for the inhibitor test. A content of 5.0 SIU/ml was found in the solution. This is 6.24 MSIU or 7.7% of the starting activity, relative to the total mixture. The resin with the adsorbed amino-sugar derivative is separated off from the fermentation broth via a sieve screw centrifuge and is simultaneously washed with deionised water on the same centrifuge. The fermentation broth and the wash water were discarded. The ion exchange resin mixture was collected, and 300 l (215 kg) were obtained. For testing, 10 g of the exchange resin mixture were eluted in an acid using 120 ml of 1 M sodium chloride solution. 115 ml of eluate were obtained, with a content of 26.9 SIU/ml. This gives, for the 10 g sample, 3,094 SIU, and for the total amount, 66.5 MSIU or 82% of the content in the fermentation broth.

Elution and Desalination

The following experiments were carried out using a combination of 2 or 3 columns connected in series. The solution used for the elution was pumped through at a rate of about 70 ml/hour. The eluate was collected in fractions and first tested qualitatively, with the aid of thin layer chromatography, for the presence of the saccharase inhibitor. The desalinated fractions containing the inhibitor were combined and tested quantitatively for their inhibitor content. The conductivity was used as a measure of the salt content. Fractions with a conductivity below 1.5 mS·cm$^{-1}$ at room temperature were considered desalinated.

EXAMPLE 6

60 g of the exchange resin mixture, with the adsorbed inhibitor (309 SIU/g), obtained according to Example 5 were filled into a column with a diameter of 2 cm and a height of 30 cm. The outlet of the column was connected to a 2nd column with a diameter of 2 cm and a height of 20 cm, which contained at the bottom a layer of 5 g of Lawatit ® MP 62 in the basic form and over this a layer of 20 g of Lewatit ® S 100 in the acid form. The direction of flow in both columns is from the top downwards. The runnings were collected in fractions and the conductivity of the solution was measured. For the elution, a solution of 1.5 l of 0.025 M calcium acetate, 0.025 M acetic acid was discharged onto the 1st column. Fractions 20–40 (358 ml) contained the inhibitor in a concentration of 31.5 SIU/ml and the conductivity was 0.325 mS·cm$^{-1}$ at pH 4.54. The total amount of inhibitor eluted was 11,277 SIU, that is to say 61% of the starting amount of 18,540 SIU.

EXAMPLE 7

Column 1: 60 g of the exchange resin mixture, with the adsorbed inhibitor (309 SIU/g), obtained according to Example 5.

Column 2: Lower layer, 5 g of Lewatit ® MP 62 (basic form), upper layer, 20 g of Lewatit ® S 100 (acid form).

Eluting agent: 0.025 M calcium acetate, 0.025 M ammonia.

Procedure as in Example 6.

Fractions 1–36 were combined (620 ml), conductivity 0.31 mS·cm$^{-1}$ at pH 4.28, inhibitor content 17 SIU/ml, that is to say 10,540 SIU or 57% of the inhibitor contained in the exchange resin mixture.

EXAMPLE 8

Column 1: 60 g of the exchange resin mixture, with the adsorbed inhibitor, obtained according to Example 5.

Column 2: Lower layer, 5 g of Lewatit ® MP 62 (basic form), upper layer, 20 g of Lewatit ® S 100 (acid form).

Eluting agent 0.05 M ammonia.

Procedure according to Example 6.

Fractions 1–36 were combined (630 ml), conductivity 0.29 mS·cm$^{-1}$ at pH 5.23, inhibitor content 17 SIU/ml, that is to say 10,710 SIU or 58% of the inhibitor contained in the exchange resin mixture.

EXAMPLE 9

Column 1: 60 g of the exchange resin mixture, with the adsorbed inhibitor, obtained according to Example 5.

Column 2: Lower layer, 4 g of Lewatit ® MP 62 (basic form), upper layer, 12 g of Lewatit ® S 100 (acid form).

Eluting agent 0.025 M calcium acetate, 0.01 M ammonia.

Procedure according to Example 6.

Fractions 1–36 were combined (625 ml), conductivity 0.23 mS·cm$^{-1}$ at pH 4.57, inhibitor content 19 SIU, ml, that is to say 11,875 SIU or 64% of the inhibitor contained in the exchange resin mixture.

EXAMPLE 9a

Column 1: 60 g of the exchange resin mixture, with the adsorbed inhibitor, obtained according to Example 5.

Column 2: lower layer: 3 g of Lewatit ® MP 62 (basic form), upper layer: 9 g of Lewatit ® S 100 (acid form).

Eluting agent 0.1 M sodium acetate solution.

Procedure according to Example 6.

Fractions 1–33 were combined (577 ml).

Conductivity 0.52 mS·cm$^{-1}$ at pH 3.9.

Inhibitor content 24 SIU/ml, that is to say 13,848 SIU or 75% of the inhibitor contained in the exchange resin mixture.

EXAMPLE 10

Column 1: 60 g of the exchange resin mixture, with the adsorbed inhibitor, obtained according to Example 5.

Column 2: Lower layer, 3 g of Lewatit ® MP 62 (basic form), upper layer, 9 g of Lewatit ® S 100 (acid form).

Eluting agent 0.035 M calcium acetate, 0.01 M ammonia.

Procedure according to Example 6.

Fractions 1–32 were combined (557 ml), conductivity 0.45 mS·cm$^{-1}$ at pH 4.6, inhibitor content 26 SIU/ml, that is to say 14,482 SIU or 78% of the inhibitor contained in the exchange resin mixture.

In order to isolate the inhibitor, the solution was freeze-dried. 1.3 g of a substance with a specific activity of 11 SIU/mg was obtained.

Elution and Desalination with Subsequent Chromatography

Example 6-10 served to determine the advantageous nature of eluting and desalinating the inhibitor. For further purification, a further column for chromatography of the inhibitor can be connected directly to the columns of Examples 6-10.

EXAMPLE 11

3 Columns, connected in series, having the following packing were used.

1st column: Diameter 15 cm, height 60 cm, 6.86 kg of the exchange resin mixture according to Example 5 with the adsorbed inhibitor (2.12 MSIU).

2nd column: Diameter 10 cm, height 60 cm, lower layer, 0.66 kg of Lewatit ® MP 62 (basic form) upper layer, 2.00 kg of Lewatit ® S 100 (acid form).

3rd column: Diameter 10 cm, height 100 cm, 4.0 kg of Lewatit ® TSW 40 (acid form).

Elution solution: 80 l of 0.35 M calcium acetate, 0.01 M ammonia.

Flow direction in all columns from the top downwards.

The elution solution was pumped onto column 1 at a rate of 5 l/hour. The runnings from column 3 were discarded. The conductivity and the pH were meansured on the running from the 2nd column, after the desalination. When the conductivity rises above 1.5 mS·cm$^{-1}$ after about 12-14 hours the entire inhibitor has been discharged onto column 3. Addition of the elution solution is stopped, column 3 is separated from the preceding column and is washed with 5 l of desalinated water. Purification of the inhibitor by chromatography in column 3 then follows, by pumping 0.025 N hydrochloric acid onto the column at 5 l/hour. The eluate is collected in fractions. The elution of the inhibitor can be observed by a precise conductivity measurement or by a differential refractometer. The fractions, each of about 9 l, were examined by thin layer chromatography for the presence of the inhibitor and its homologues, and the suitable fractions (14-17) were combined. 36 l were obtained, with an inhibitor content of 46 SIU/ml, that is to say 1.66 MSIU or 78% of the inhibitor content of the exchange resin mixture.

For further working up, the pH value of the solution was increased to 6.5 using Lawatit ® M 600 (basic form) and the solution was then filtered off, concentrated to 2.65 l in vacuo and freeze-dried. 22.2 of the inhibitor were obtained with a specific activity of 67 SIU/mg, that is to say 1.49 MSIU or 70% of the inhibitor content of the exchange resin mixture or 58% of the inhibitor content of the fermentation broth.

EXAMPLE 12

1,600 l of a fermentation broth with a mycelium content of 27% corresponding to a solution volume of 1,168 l, had a saccharase inhibitor content of 68 SIU/ml. The total content is thus 79.4 MSIU. 250 l of Lewatit ® SC 104 (acid form) and 120 l of Lewatit ® MP 62 (basic form) were introduced into the stirred fermentation broth in the course of 1 hour. The mixture is subsequently stirred for a further 2 hours and a sample was then taken. An inhibitor content of 7.4 SIU/ml was found in the solution. Thus in the total mixture 8.6 MSIU were not adsorbed (11%).

The ion exchange resin mixture with the adsorbed active compound was separated off from the fermentation broth via a sieve screw centrifuge and simultaneously washed with deionised water. The fermentation broth was discarded. The ion exchange resin mixture (390 l) was collected and filled into a 500 l kettle. A suction head with nozzle sieves, which later allowed the solution to be filtered off, had first been fitted at the lowest point of the kettle. The air in the resin was displaced by adding deionised water at the bottom. The suction line of the kettle was connected, via a pump and a rotameter, to a column of diameter 30 cm and height 150 cm, which contained 76 l of Lewatit S 100 (acid form). The outflow of this column was connected with a 2nd column (diameter 30 cm, height 100 cm) which was filled with 32 l of Lewatit ® MP 62 (basic form). The outflow from the 2nd column passes to the separation column (diameter 20 cm, height 150 cm), which contained 76 l of Lewatit ® TSW 40 (acid form).

The elution solution, consisting of 200 l of 0.1 M sodium acetate, was discharged onto the top of the resin in the kettle at the same rate (80 l/hour) as the solution was removed from the bottom via the suction head, using the pump. The solution flows through the kettle and the columns successively until the conductivity measured after the 2nd column (MP 62 column) exceeds 1.5 mS.cm$^{-1}$. The inhibitor is then on the separation column. This is separated from the other columns and itself rinsed with 20 l of deionised water and the inhibitor is chromatographed with 1,600 l of 0.025 M hydrochloric acid. The rate of elution was reduced to 40 l/hour. The eluate was collected in fractions. The fractions were examined by thin layer chromatography for the amino-sugar derivative and appropriately combined. A main fraction of 220 l was obtained which contained 236 SIU/ml. (51.9 MSIU; 65% of the content of the fermentation solution).

Lewatit ® M 600 (basic form) was added to the main fraction in a 500 l stirred kettle until a pH value of 5.0 was achieved. The solution was filtered over a suction head with nozzle sieves into a distillation vessel, the exchange resin was rinsed with 40 l of deionised water, and the solution was concentrated to 20 l in vacuo. The concentrate had a conductivity of 4.5 mS.cm$^{-1}$ and was desalinated to 1.2 mS.cm$^{-1}$ and brought to a pH value of 6.0 by adding Lewatit ® S 100 (acid form) and Lewatit ® M 600 (basic form). The solids were filtered off and the solution was filtered through a sterile filter and freeze-dried.

Yield 631 g specific activity 65 SIU/mg, total activity: 41 MSIU 52% of the content of the fermentation solution.

What is claimed is:

1. A process for isolating an amino sugar derivative which is 0-{4,6-dideoxy-4[[1S-(1,4,6/5)-4,5,6-trihydroxy-3-hydroxymethyl-2-cyclohexen-1-yl]-amino]-α-D-glucopyranosyl}-(1→4)-0-α-D-glucopyranosyl-(1→4)-D-gluco pyranose from a culture broth obtained by fermenting a micro-organism of the family Actinoplanaceae which comprises
   (a) adding a mixture of a strongly acid cation exchange resin and an anion exchange resin in the acid or basic form to the said culture broth,
   (b) separating the resin mixture from the culture filtrate and from any mycelium that may be present, (c) treating the separated off resin mixture with at least one cation containing dilute solution so as to elute the amino-sugar derivative, (d) passing the resulting eluate over a combination of a highly crosslinked strongly acid cation exchanger, which weakly bonds the amino-sugar derivative in the H⊕ form and an anion exchanger in the basic form, (e) passing the eluate over a strongly acid cation exchanger, which bonds the amino-sugar derivative strongly in the H⊕ form, (f) treating the cation exchanger with the amino-sugar derivative bonded thereto with from 0.01 to 0.05 N mineral acid so as to fractionally elute material bound to the exchanger in a plurality of fractions, and then (g) recovering the fraction(s) containing said amino-sugar derivative.

2. A process according to claim 1 in which the microorganism is a strain belonging to the genus Actinoplanes.

3. A process according to claim 1 in which the resin mixture is added to the culture broth without the mycelium having been previously separated therefrom.

4. A process according to claim 1 in which the resin mixture is washed after separation from the culture filtrate.

5. A process as claimed in claim 1 in which the cation exchanger with the amino-sugar bonded strongly thereto is washed prior to the mineral acid treatment.

6. A process as claimed in claim 5 in which water is used for the washing.

7. A process as claimed in claim 1 in which the amino-sugar derivative containing fraction(s) is (are) brought to a pH of from 5 to 7.

8. A process as claimed in claim 7 in which the resulting fractions are concentrated, filtered and dried.

9. A process as claimed in claim 1 in which the strongly acid cation exchange resin which bonds the amino-sugar derivative strongly is a polystyrene resin and is crosslinked to the extent of from 2 to 6%.

10. A process as claimed in claim 1 in which the highly crosslinked cation exchanger which weakly bonds the amino-sugar derivative is polystyrene-based and is crosslinked to the extent of from 7 to 20%.

11. A process according to claim 1 in which the cation exchanger is eluted in process step (f) with from 0.01 to 0.1 N hydrochloric acid.

12. A process according to claim 1 in which in process step (c), the elution is carried out with a dilute salt solution.

13. A process as claimed in claim 12 in which the salt solution comprises a solution of an alkali metal salt, alkaline earth metal salt and/or ammonium salt of a weak acid.

14. A process according to claim 13 in which dilute sodium acetate solution is used.

15. A process according to claim 14 in which sodium acetate solution having a concentration in the range of from 0.05 to 0.2 M is used.

16. A process according to claim 13 in which an alkaline earth metal salt solution having a concentration in the range of from 0.025 to 0.10 M is used.

17. A process for adsorbing an amino-sugar derivative which is 0-{4,6-dideoxy-4[[IS-(1,4,6/5)-4,5,6-trihydroxy-3-hydroxymethyl-2-cyclohexen-1-yl]-amino]-α-D-glucopyranosyl}-(1→4)-0-α-D-glucopyranosyl-(1→4)-D-gluco pyranose from a culture broth obtained by fermenting a micro-organism of the family Actinoplanaceae which comprises adding a mixture of a strongly acid cation exchange resin and an anion exchange resin in the acid or basic form to said culture broth, then separating said resin mixture from the culture-filtrate and from any mycelium that may be present.

* * * * *

UNITED STATES PATENT AND TRADEMARK OFFICE
CERTIFICATE OF CORRECTION

PATENT NO. : 4,174,439

DATED : November 13, 1979

INVENTOR(S) : Erich Rauenbusch, et al.

It is certified that error appears in the above-identified patent and that said Letters Patent are hereby corrected as shown below:

Column 7, line 7, after "H" insert --$^+$--.

Signed and Sealed this

Twenty-sixth Day of February 1980

[SEAL]

Attest:

SIDNEY A. DIAMOND

Attesting Officer     Commissioner of Patents and Trademarks